United States Patent

Das

Patent Number: 4,542,151
Date of Patent: Sep. 17, 1985

[54] TETRAHYDROTHIENYL SUBSTITUTED ETHERS

[75] Inventor: Jagabandhu Das, Plainsboro, N.J.

[73] Assignee: E. R. Squibb & Sons, Inc., Princeton, N.J.

[21] Appl. No.: 682,712

[22] Filed: Dec. 17, 1984

[51] Int. Cl.$^4$ .................. A61K 31/38; C07D 333/24
[52] U.S. Cl. ...................................... 514/438; 549/79
[58] Field of Search ........................ 514/438; 549/79

[56] References Cited

U.S. PATENT DOCUMENTS

| | | |
|---|---|---|
| 4,143,054 | 3/1979 | Sprague . |
| 4,187,236 | 2/1980 | Sprague . |
| 4,220,594 | 9/1980 | Sprague . |
| 4,228,180 | 10/1980 | Sprague . |
| 4,254,044 | 3/1981 | Sprague . |

FOREIGN PATENT DOCUMENTS 0043292  8/1982  European Pat. Off. .
2039909  8/1980  United Kingdom .

Primary Examiner—Alan Siegel
Attorney, Agent, or Firm—Lawrence S. Levinson; Burton Rodney

[57] ABSTRACT

Tetrahydrothienyl substituted ethers are provided having the structural formula

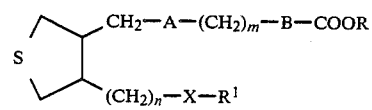

wherein A is $(CH_2)_2$, CH=CH or a single bond, m is 1 to 5, B is a single bond or CH=CH, n is 1 to 4, X is O or

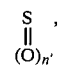

wherein n' is 0, 1 or 2, R is H, lower alkyl or alkali metal and $R^1$ is lower alkyl, arylalkyl, aryl, cycloalkyl, cycloalkylalkyl or lower alkenyl and including all stereoisomers thereof.

The compounds are cardiovascular agents useful, for example, in the treatment of thrombolytic disease and as antiinflammatory agents and analgesics.

18 Claims, No Drawings

TETRAHYDROTHIENYL SUBSTITUTED ETHERS

DESCRIPTION OF THE INVENTION

The present invention relates to tetrahydrothienyl substituted ethers which are cardiovascular agents useful, for example, in the treatment of thrombolytic disease. These compounds have the general formula

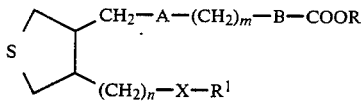

(including all stereoisomers thereof) wherein A is $(CH_2)_2$—, —CH=CH— or a single bond; m is 1 to 8; B is a single bond or —CH=CH—; R is H, lower alkyl or alkali metal; n is 1 to 4, X is —O— or

wherein n' is 0, 1 or 2; and $R^1$ is lower alkyl, arylalkyl, aryl, cycloalkyl, cycloalkylalkyl or lower alkenyl. The term "lower alkyl" or "alkyl" as employed herein by itself or is part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent (for example,

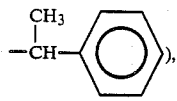

an alkyl-aryl substituent, a haloaryl substituent, a cycloalkyl substituent or an alkylcycloalkyl substituent.

The term "cycloalkyl" by itself or is part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein by itself or is part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "lower alkenyl" or "alkenyl" by itself or is part of another group includes straight or branched chain radicals of from 2 to 12 carbons, preferably 2 to 6 carbons in the normal chain, which include one double bond in the normal chain, such as 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "aralkyl", "aryl-alkyl" or "aryl-lower alkyl" as used herein by itself or is part of another group refers to lower alkyl groups as discussed above having an aryl substituent, such as benzyl or methylbenzyl

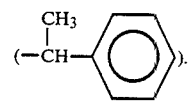

The term "cycloalkylalkyl" as used herein by itself or is part of another group refers to cycloalkyl groups as defined above linked to an alkyl group as defined above.

The term "lower alkoxy", "alkoxy" or "aralkoxy" by itself or is part of another group includes any of the above lower alkyl, alkyl or aralkyl groups linked to an oxygen atom.

The term "halogen" or "halo" as used herein by itself or is part of another group refers to chlorine, bromine, fluorine or iodine with chlorine being preferred.

The term "$(CH_2)_m$", $(CH_2)_n$, and "$(CH_2)_2$" includes straight or branched chain radicals having from 1 to 8 carbons and 1 to 4 carbons in the normal chain in the case of $(CH_2)_m$, and $(CH_2)_n$, respectively, and 2 carbons in the normal chain in the case of $(CH_2)_2$, and may contain one or more lower alkyl substituents. Examples of $(CH_2)_m$, $(CH_2)_n$ and $(CH_2)_2$ groups include $CH_2$,

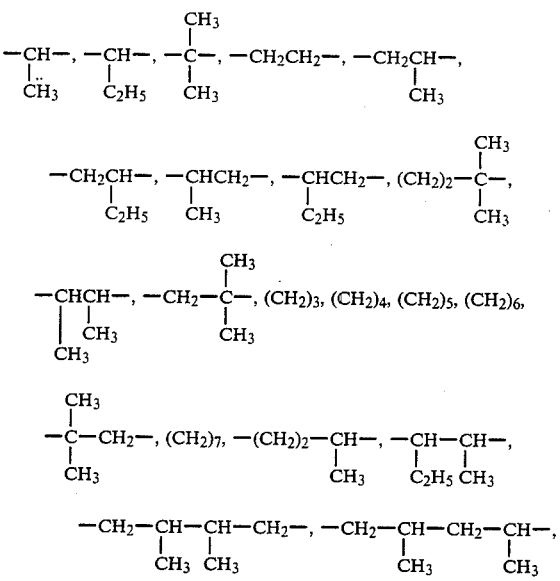

and the like.

Preferred are those compounds of formula I wherein A is —CH=CH— or —$(CH_2)_2$—, B is a single bond, m is 2 or 5, n is 1 or 2, R is hydrogen and $R^1$ is lower alkyl, phenyl, cycloalkyl or benzyl.

Compounds of formula I of the invention of the cis series may be prepared using aldehyde II as the starting material

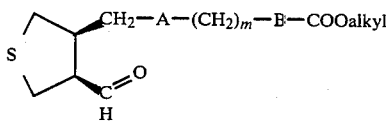

Thus, to prepare compounds of formula I wherein X is O, B is a single bond, A is CH=CH or (CH₂)₂ and n is 1, aldehyde II is reduced by treating II with a reducing agent such as sodium borohydride, or sodium cyanoborohydride in an inert organic solvent, such as methanol, to form alcohol III

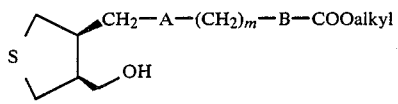

Alcohol III is then made to undergo ether formation by reacting III with a compound of the structure IV

Y-R¹      IV wherein Y is Cl, Br, I, —OSO₂CH₃ or

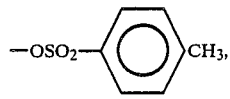

in the presence of potassium hydroxide or other strong base and an inert organic solvent such as xylene, tetrahydrofuran (THF), dimethylsulfoxide (DMSO) or dimethylformamide (DMF) employing a molar ratio of III:IV of within the range of from about 0.2:1 to about 0.1:1, to form V

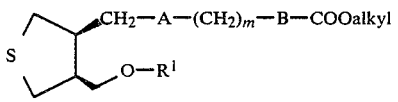

Where in formula IV, X is Br or Cl, a phase transfer etherification is employed in which case THF is used as the solvent and a transfer reagent such as (C₄H₉)₄NHSO₄ or (C₆H₅CH₂)(CH₃)₂NHSO₄ is employed.

The ester V may then be hydrolyzed by treatment with a strong base such as lithium hydroxide, potassium carbonate or sodium hydroxide in the presence of an inert organic solvent such as tetrahydrofuran to form the corresponding alkali metal salt which is treated with a strong acid, such as HCl, to form the cis compounds of the invention

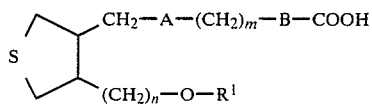

Compounds of formula I of the invention of the trans series wherein X is O, and B is a single bond, may be prepared using aldehyde IIA

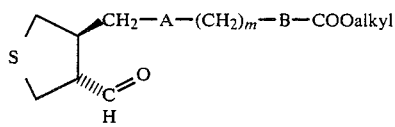

which itself is prepared from aldehyde II by simply subjecting II to an epimerization reaction wherein II is reacted with sodium methoxide in the presence of methanol to form aldehyde IIA.

Aldehyde IIA is then reduced by treatment with sodium borohydride or sodium cyanoborohydride in the presence of an inert organic solvent such as methanol to form alcohol VI

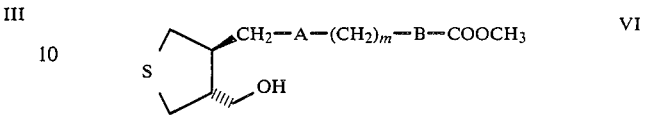

which is then etherified by reaction with a mesylate, tosylate or halide IV

Y-R¹      IV as described above with respect to the cis series to form ester VII

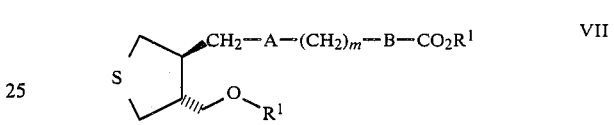

Ester VII is then hydrolyzed by treatment with a strong base such as lithium hydroxide, potassium carbonate or sodium hydroxide in the presence of an inert organic solvent such as tetrahydrofuran, to form the corresponding alkali metal salt which is treated with a strong acid, such as HCl, to form the trans compounds of the invention VIII

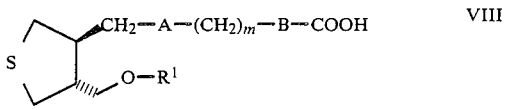

Compounds of the invention wherein X is S may be prepared from hydroxymethyl compound III or VI. Thus, where A is —CH=CH— and B is a single bond, compound III or VI is subjected to a tosylation reaction, for example, by reacting III or VI with tosyl chloride in pyridine to form tosylate IX

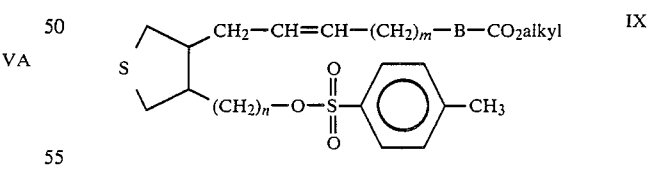

To form the tosylate IXA (where A is (CH₂)₂, compound III or VI is reduced, for example, with hydrogen over a palladium on carbon catalyst, to form hydroxymethyl compound IIIA or VIA (where A is (CH₂)₂)

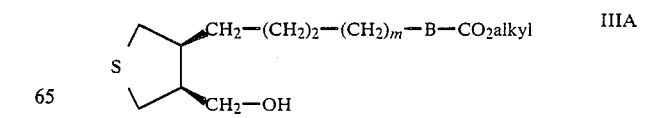

or

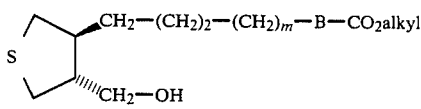   VIA

Compound IIIA or VIA is subjected to a tosylation reaction to form tosylate IXA (where A is (CH₂)₂)

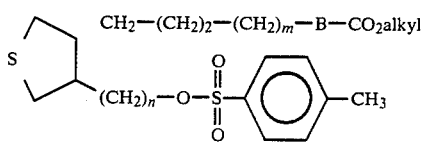   IXA

Thereafter, tosylate IX or IXA is reacted with a thiol of the structure

R¹SH    X employing a molar ratio of IX or IXA:thiol of within the range of from about 0.8:1 to about 1:1, in a solvent such as tetrahydrofuran and in the presence of potassium t-butoxide to form the sulfide XI or XIA

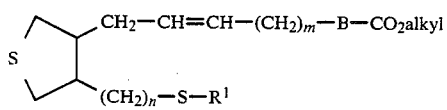   XI

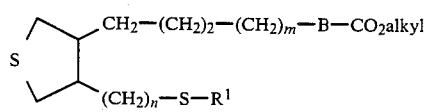   XIA

To form the sulfinyl and/or sulfonyl analogs (where n'=1), sulfide derivative XI or XIA is subjected to oxidation, for example, by reacting same with sodium periodate, in the presence of methanol and tetrahydrofuran, to form the sulfinyl derivative XII or XIIA and the sulfonyl derivative XIII or IIIA. The sulfinyl and sulfonyl derivatives may be separated by chromatography or other conventional separation procedures.

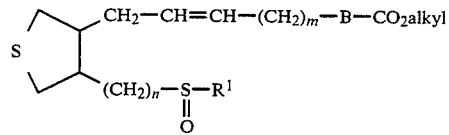   XII

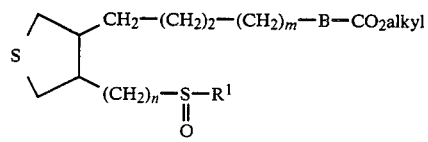   XIIA

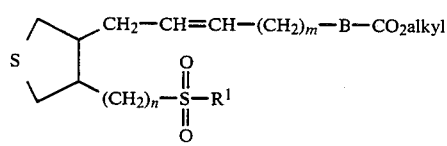   XIII

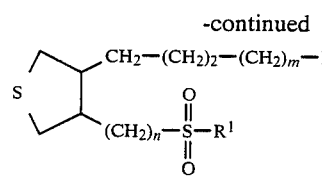   XIIIA

Compounds of Formula I wherein n is 2 to 4, may be prepared starting with the starting lower alkyl ester containing the hydroxymethyl group, that is, compound III or VI which is used to form the aldehyde II' (where A is —CH=CH—) or II" (where A is —(CH₂)₂).

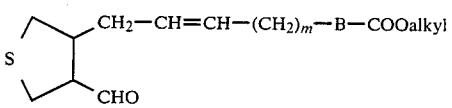   II'

(includes cis and/or trans)

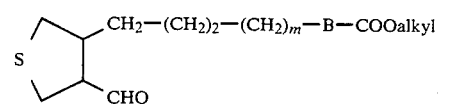   II"

Thus, to form aldehyde II' where A is —CH=CH—, compound III or VI is subjected to a Collins oxidation, for example, by reacting III or VI with chromium trioxide in pyridine. To form the aldehyde II" (where A is (CH₂)₂), compound III or VI is reduced, for example, with hydrogen over a palladium on carbon catalyst, to form hydroxymethyl compound IIIA or VIA as described above and compound IIIA or VIA is subjected to a Collins oxidation to form aldehyde II" (where A is (CH₂)₂ including all isomers).

The aldehyde II' or II" is used to prepare aldehyde XV (where n is 2–4) by carrying out a homologation sequence, such as a Wittig reaction with (C₆H₅)₃P=CHOMe followed by hydrolysis, (n−1) times, as shown below.

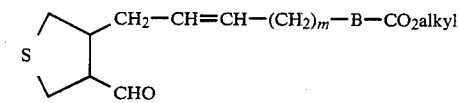

II' or

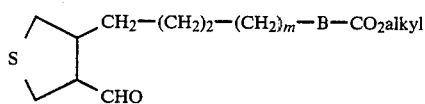

II"

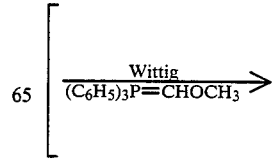

-continued

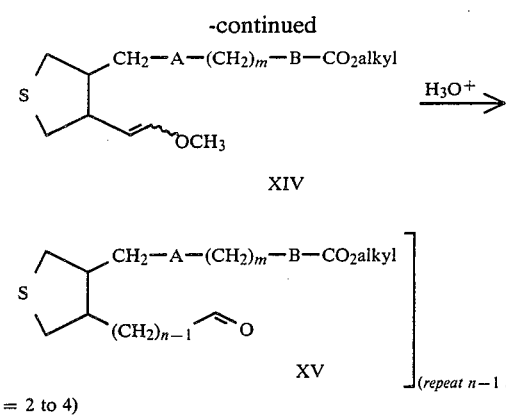

(n = 2 to 4)

The aldehyde XV (where n is 2–4) is thus carried on to compounds of this invention where n is 2–4, that is

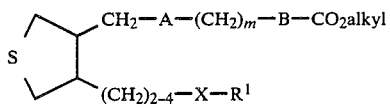

(IA where A is —CH=CH—)
(IB where A is (CH$_2$)$_2$)

by reducing aldehyde XV employing a reducing agent such as sodium borohydride or sodium cyanoborohydride in a solvent such as methanol to form the alcohol ester XVI

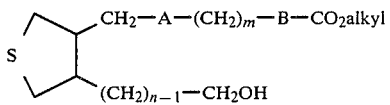

which is subjected to a tosylation/mesylation reaction as described above to form the corres-ponding tosylate/mesylate which in turn is subjected to ether formation by reaction with

Y-R$^1$      IV or

R$^1$SH      A as described above to form ether IC or thioether ID

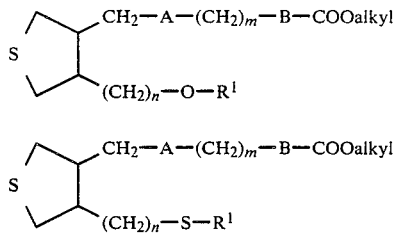

The sulfinyl derivatives (where n is 2 to 4) and sulfonyl derivatives (where n is 2 to 4) are prepared by subjecting thioether ID (n'=0) to an oxidation reaction as described above to form a mixture of sulfinyl (n'=1) and sulfonyl derivatives (n'=2).

The above sulfinyl and sulfonyl derivatives may be separated by chromatography or other conventional separation procedures.

The various esters XI, XIA, XII, XIIA, XIII, XIIIA, IA, IB, IC, and ID can be converted to the free acid, that is, to

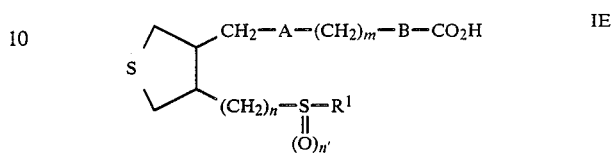

by treatment of the esters with an alkali metal hydroxide, such as lithium or sodium hydroxide to form the alkali metal salt, followed by neutralization with an acid, such as dilute hydrochloric acid or oxalic acid to form the acid IE.

Compounds of the invention wherein B is —CH=CH— and A is CH=CH or (CH$_2$)$_2$ may be prepared as follows. The tetrahydrofuranyl ether or thio ether of the structure XVII

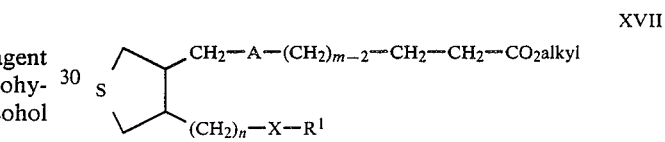

is subjected to phenylselenylation by reacting XVII with lithium temperatures of from about 0 to about −78° C. in the presence of an inert organic solvent such as tetrahydrofuran, dimethoxy ethane or ether; thereafter a solution of diphenyl-diselenide in an inert organic solvent as described above is added and the reaction is maintained at reduced temperatures as described above to form the selenophenyl ester XVIII

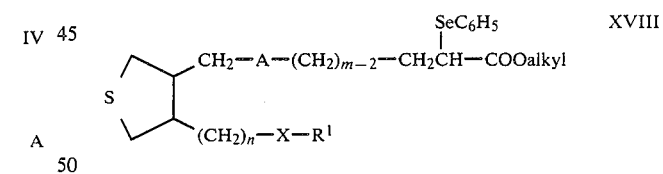

The selenophenyl ester XVIII is next hydrolyzed by reaction with a strong base such as LiOH, K$_2$CO$_3$ or NaOH and then treated with strong acid such as HCl as described hereinbefore to form acid XIX

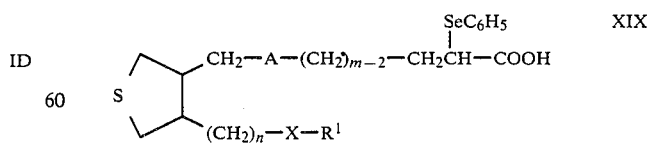

The selenophenyl acid XIX is then made to undergo a selenoxide elimination reaction wherein the selenophenyl acid is treated with hydrogen peroxide in an inert organic solvent such as tetrahydrofuran to form acid XX

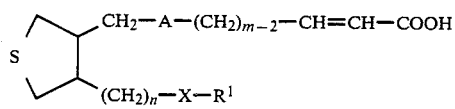  XX

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The aldehyde intermediate II

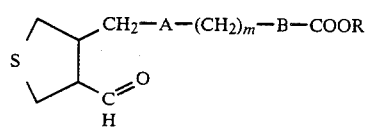  II wherein A is —CH=CH may be prepared as follows.

1-Trimethylsilyloxy-1,3-butadiene A in an inert organic solvent such as methylene chloride, ether or tetrahydrofuran is made to react with maleic anhydride B in a Diels-Alder reaction to form the anhydride C

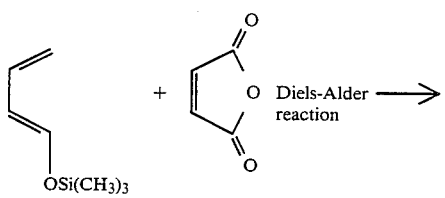

The anhydride C is treated with concentrated hydrochloric acid in the presence of an inert organic solvent such as tetrahydrofuran to form the desilylated adduct D

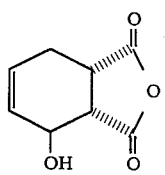  D which is then reacted with dihydropyran in the presence of dry methylene chloride and p-toluenesulfonic acid to form the tetrahydropyranyl ether E

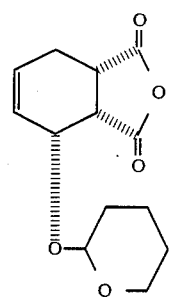  E

The ether E is reduced, for example, by treatment with a reducing agent such as lithium aluminum hydride, in the presence of an inert organic solvent such as tetrahydrofuran to form diol F

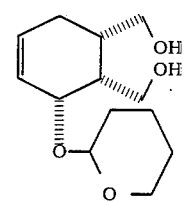  F

The diol F is then reacted with dimethylamino pyridine and methyl chloroformate in the presence of an inert organic solvent such as methylene chloride and a base such as pyridine to form bis-methylcarbonate G

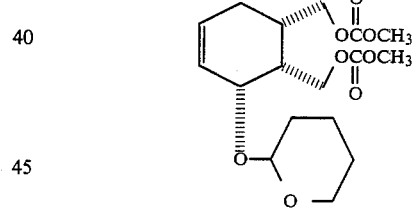  G which is then made to undergo osmylation by reacting G with osmium tetroxide in the presence of N-methylmorpholine-N-oxide and appropriate inert organic solvent such as tetrahydrofuran to form diol H

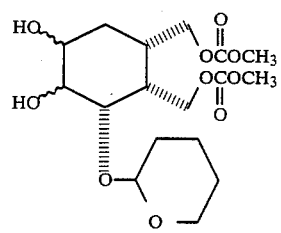  H

The diol H is next subjected to periodate cleavage by reacting diol H in an alcohol solvent such as methanol with sodium metaperiodate to form dialdehyde J

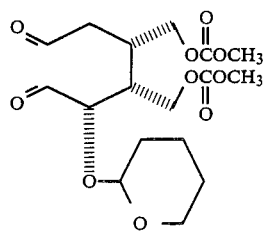
J

The dialdehyde J is then reduced by treatment with a reducing agent such as sodium borohydride or lithium borohydride in the presence of an inert organic solvent such as methanol or tetrahydrofuran, to form the diol K

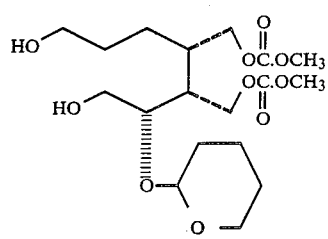
K which is then subjected to acetonide formation by treating K with dry Amberlyst-15 acid resin in the presence of methanol and acetone to form the alcohol L

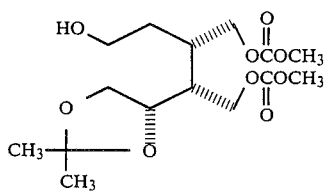
L which is treated with p-toluenesulfonic acid and dihydropyran in the presence of an inert organic solvent such as methylene choride, to form tetrahydropyranyl ether M

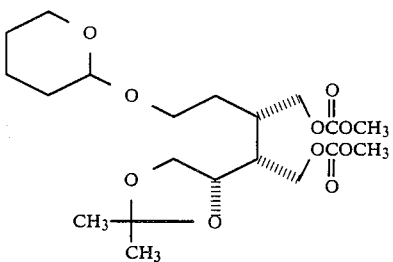
M which is then reduced to the diol N by treating M with lithium aluminum hydride in the presence of an inert solvent such as tetrahydrofuran

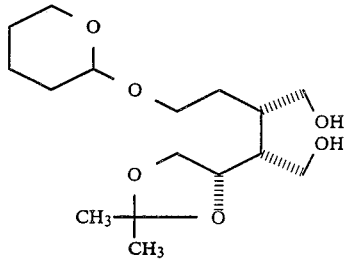
N

The diol N is then reacted with methanesulfonyl chloride in the presence of an organic solvent such as pyridine to form the bis-mesylate O

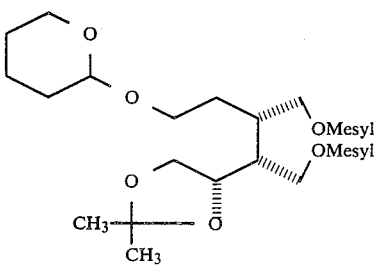
O

The bis-mesylate O in dimethylsulfoxide or methanol is treated with sodium sulfide nonahydrate in dimethyl sulfoxide or methanol to form the tetrahydrothiophane P

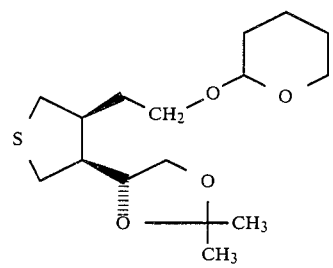
P which is treated with Amberlyst-15 resin in the presence of methanol and acetone to form the alcohol Q

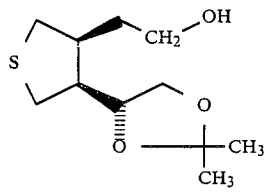
Q

Alcohol Q is then treated with dimethylsulfoxide in the presence of oxalyl chloride and methylene chloride and then with triethylamine to form the aldehyde R

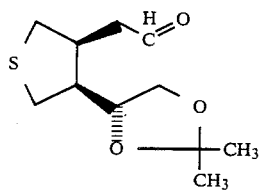

R

Aldehyde R is next subjected to a Wittig reaction wherein a mixture of triphenylphosphonium compound S

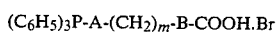

such as (4-carboxybutyl)-triphenylphosphonium bromide salt in tetrahydrofuran and potassium t-amylate in toluene is reacted with aldehyde R to form acid T

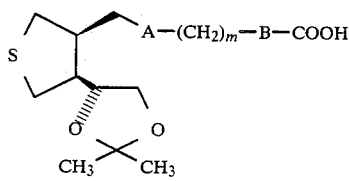

T which is then dissolved in ether and reacted with a diazoalkane such as diazomethane to form ester U

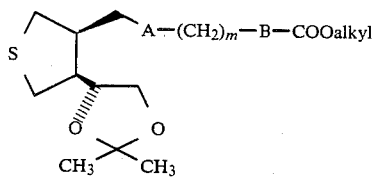

U

Ester R is then made to undergo acetal exchange by reacting R in methanol with p-toluene sulfonic acid to form diol V

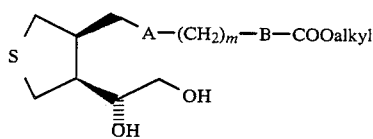

V which is then subjected to periodate cleavage by reacting S in methanol with sodium metaperiodate to form aldehyde IIA

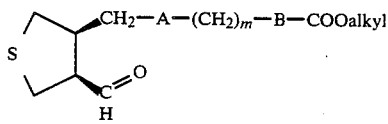

IIA (wherein A is CH=CH)

The intermediate aldehyde of formula II wherein A is —(CH₂)₂— are prepared by reducing compound V by treatment with hydrogen in the presence of palladium on charcoal to form compound V'

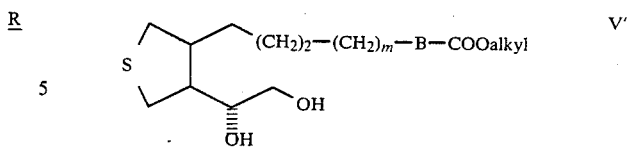

V' which is subjected to periodate cleavage as described above to form aldehyde IIAA

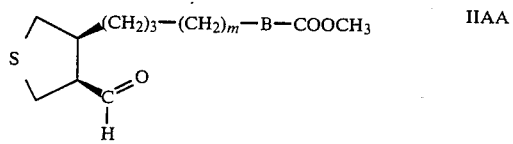

IIAA which may then be hydrolyzed to the corresponding acid XIX by treatment with alkali metal hydroxide and then HCl as described hereinbefore.

The compounds of this invention have three centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis and trans forms and stereoisomeric pairs may be prepared as shown in the working Examples which follow. Examples of such stereoisomers are set out below.

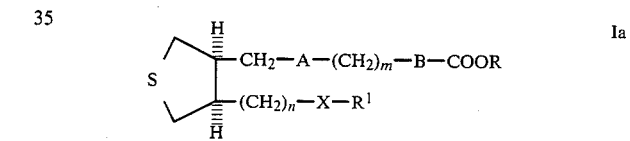

Ia (cis)

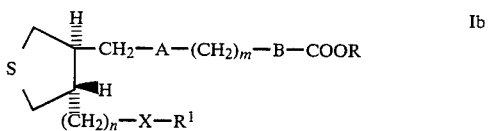

Ib (trans)

The compounds of this invention are cardiovascular agents useful as platelet aggregation inhibitors, such as inhibiting arachidonic acid-induced platelet aggregation (e.g., for treatment of thrombolytic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors. In addition, the compounds of the invention are useful as analgesic agents in the manner of aspirin and indomethacin in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of this invention when used in combination with a cyclic AMP phosphodiesterase inhibitor such as theophylline or papaverine may be used in the preparation and to prolong storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention. Unless otherwise indicated, all temperatures are expressed in degrees Centigrade.

EXAMPLE 1

[3α(Z),4α]-7-[4-[(Hexyloxy)methyl]tetrahydro-3-thienyl]-5-heptenoic acid

A.
[3α(Z),4α]-7-[Tetrahydro-4-formyl-3-thienyl]-5-heptenoic acid, methyl ester (1) (1α,2β,3β)-1-Trimethylsilyloxy-cyclohex-5-ene, 2,3-dicarboxylic acid anhydride To a solution of 23.6 ml of 1-trimethylsilyloxybutadiene (133.33 mmol) in 200 ml of dry methylene chloride was added with stirring 10 g of maleic anhydride (100 mmole). The homogeneous reaction mixture was stirred at room temperature for 24 hours, whereupon most of the methylene chloride was removed by distillation under reduced pressure. The crude oil was presoaked in silica gel and loaded on a 200 g silica gel column. Elution with 10–25% ethyl acetate in hexane and finally with 50% ethyl acetate in hexane gave 23.13 g of desired title adduct as a colorless oil.

(2)
(1α,2β,3β)-1-Hydroxy-cyclohex-5-ene2,3-dicarboxylic acid anhydride

To a solution of 10 g of Part (1) tri-methylsilyloxy adduct (41.7 mmole) in 50 ml of distilled THF was added with stirring 1 ml of concentrated hydrochloric acid. The reaction mixture was stirred at room temperature for 2 hours, whereupon it was filtered through a pad of anhydrous magnesium sulfate. The filtrate was concentrated under reduced pressure to obtain the title desilylated adduct.

(3)
(1α,2β,3β)-1-Tetrahydropyranyloxycyclohex-5-ene-2,3-dicarboxylic acid anhydride The crude Part (2) desilylated adduct was dissolved in 50 ml of dry methylene chloride and cooled in an ice-water bath. To this solution was added 5.6 ml of reagent grade dihydropyran, followed by 30 mg of p-toluene sulfonic acid. After stirring for 1 hour at 0°–5° C., the reaction mixture was washed with saturated sodium bicarbonate solution. The aqueous layer was extracted with ether. The combined organic extract was dried over anhydrous magnesium sulfate and concentrated under reduced pressure. The crude residue was chromatographed on a silica gel column and eluted with 10–20% ethyl acetate in hexane to obtain 9.33 g of desired title tetrahydropyranyl ether as a colorless oil (93% yield).

(4)
(1α,2β,3β)-1-Tetrahydropyranyloxycyclohex-5-ene-2,3-dimethanol

To a suspension of 2.28 g of 95% pure lithium aluminum hydride in 300 ml of freshly distilled THF (60 mmole), cooled in an ice-water bath was added dropwise a solution of 9.33 g of Part (3) anhydride (38.2 mmole) in 50 ml of dry THF over a period of 45 minutes. After the addition was complete, the cooling bath was removed and the reaction mixture was allowed to stand at room temperature overnight, whereupon it was again placed on an ice-water bath and excess of LAH was destroyed by careful addition of freshly prepared saturated sodium sulfate solution. Addition of sodium sulfate was continued until all the lithium and aluminum salts were precipitated as a granular solid. Solid magnesium sulfate was added to the reaction mixture and it was then filtered. The residue was washed several times with methylene chloride. Finally the residue was taken up in 1000 ml of a 10% acetonitrile in ethyl acetate and stirred for 30 minutes. It was then filtered. Combined filtrate was concentrated under reduced pressure to obtain an oily residue. The crude residue was chromatographed on a silica gel column and eluted with 20–50% ethyl acetate in hexane to obtain 8.17 g of desired title diol as a viscous oil (~93% yield).

(5)
(1α,2β,3β)-1-Tetrahydropyranyloxycyclohex-5-ene-2,3-dimethanolbismethyl carbonate To a solution of 7.767 g of Part (4) diol (31.83 mmole) in 100 ml of dry methylene chloride and 10 ml of pyridine (250 mmole) cooled at 0° C. was added with stirring 390 mg of 4-dimethylamino pyridine (3.2 mmole, 10 mole %) followed by 5.8 ml of methyl chloroformate (75 mmole, 1.17 equiv) dropwise. An immediate precipitate of pyridinium hydrochloride was observed. The reaction mixture was maintained at 0° C. for additional 4 hours, whereupon it was washed thoroughly with water and then with saturated copper sulfate solution. The aqueous extracts were extracted with ether (X3). The combined organic extract was washed with water, saturated salt solution and finally was dried over magnesium sulfate. Evaporation of solvent under reduced pressure gave an oil which was chromatographed on a 250 g silica gel column and eluted with 5–15% ethyl acetate in hexane to obtain 10.87 g of desired title bis-methylcarbonate (95% yield) which solidified on standing in the cold room.

(6)
(1α,2β,3β)-1-Tetrahydropyranyloxy-5,6-dihydroxycyclohexane-2,3-dimethanolbismethyl carbonate To a solution of 5.13 g of Part (6) bis-methylcarbonate (14.25 mmole) in 30 ml of distilled THF was added with stirring 2.16 g of crystalline N-methylmorpholine N-oxide (16 mmole). Water was added dropwise to the reaction mixture, until it became homogeneous. To this homogeneous solution was now added 100 ml of a solution of osmium tetroxide (250 mg/5 ml of ether) in ether. The reaction mixture was stirred at room temperature for 30 hours, whereupon aqueous sodium bisulfate solution was added to the reaction mixture. The solution was stirred for an additional 30 minutes, whereupon the organic layer was separated and the aqueous layer was extracted several times with methylene chloride. The combined organic extract was washed with saturated salt solution, dried over anhydrous magnesium sulfate and finally was concentrated under reduced pressure. Trituration with ether gave a white precipitate which was filtered off and washed with cold-ether. 3.88 g of crystalline diol was obtained as white solid. The filtrate was concentrated under reduced pressure and the residue was chromatographed on a silica gel column. Elution with 30–50% ethyl acetate in hexane and finally with ethyl acetate gave an additional 987 mg of crystalline title diol. Total yield=4.867 g (~87% yield).

(7)
[2-(1-Formyl-methyl)-3-(1-tetrahydropyranyloxy-1-formyl-methyl)butane]-1,4-bismethyl carbonate To a solution of 3.67 g of crystalline Part (6) diol (~10 mmole) in 15 ml of methanol and 15 ml of distilled THF, cooled in an ice-water bath was added with stirring a solution of 1.75 g of powdered sodium-metaperiodate (15 mmole) in 15 ml of water. After the addition was over, the reaction mixture was stirred vigorously at 0°–5° C. for 1 hour and finally at room temperature for an additional 4 hours, whereupon TLC indicated complete disappearance of the diol. The crude reaction mixture was diluted with ether and washed thoroughly with water. The aqueous layer was reextracted with ether (X3). The combined organic extract was dried over anhydrous magnesium sulfate and finally was concentrated under reduced pressure to obtain the crude title dialdehyde as a colorless oil.

(8)
[2-(1-Hydroxymethyl-methyl)-3-(1-tetrahydropyranyloxy-1-hydroxymethylmethyl)butane]-1,4-bismethyl carbonate The crude Part (7) dialdehyde was now dissolved in 25 ml of methanol and cooled at −10° C. in a dry ice-acetone bath and 380 mg of solid sodium borohydride (10 mmole) was added in portions with stirring. After stirring at −10° C. to +5° C. for 1 hour, aqueous ammonium chloride solution was added to the reaction mixture. It was then extracted with ether (X3) and then with methylene chloride (X3). The combined organic extract was dried over anhydrous magnesium sulfate and finally was concentrated under reduced pressure to obtain 3.83 g of crude title diol as a viscous oil.

(9)
[2-(2-Hydroxyethyl)-3-(3,3-dimethyl-2,4-dioxa-cyclopentyl)-butane]-1,4-bismethyl carbonate To a solution of 3.83 g of crude Part (8) diol from the previous reaction in 20 ml of dry methanol and 20 ml of dry acetone (dried over molecular sieves) was added with stirring 800 mg of powdered and dry Amberlyst-15 acid resin. The heterogeneous reaction mixture was stirred under an argon atmosphere overnight, whereupon it was diluted with ether and filtered through anhydrous magnesium sulfate. Residual molecular Amberlyst resin was thoroughly washed with ether. The filtrate was concentrated under reduced pressure and the crude residue was chromatographed on a silica gel column. Elution with 20–50% ethyl acetate in hexane gave 2.85 g of desired title acetonide alcohol (87% overall yield from six membered Part (6) diol) as a colorless viscous oil.

(10)
[2-(2-Tetrahydropyranyloxyethyl)-3-(3,3-dimethyl-2,4-dioxa-cyclopentyl)-butane]-1,4-bismethyl carbonate To a solution of 2.65 g of Part (9) acetonide-alcohol (7.6 mmole) in 40 ml of dry methylene chloride was added with stirring at 0°−5° C. (ice-water bath) a catalytic amount of p-toluene-sulfonic acid and 750 μl of dihydropyran (8.3 mmole). The reaction mixture was stirred under dark at −0°-5° C. for 1 hour, whereupon it was washed with aqueous sodium bicarbonate solution. The aqueous layer was extracted with ether (X2). The combined organic extract was dried over anhydrous magnesium sulfate, filtered and the filtrate was concentrated under reduced pressure. The crude oily residue was chromatographed on a silica-gel column and eluted with 5–10% ethyl acetate in hexane to obtain 3.02 g of desired title tetrahydropyranyl ether which crystallized on standing at −20° C. (92% yield).

(11)
[2-(2-Tetrahydropyranyloxyethyl)-3-(3,3-dimethyl-2,4-dioxa-cyclopentyl)-butane]-1,4-diol To a suspension of 380 mg of lithium aluminum hydride (10 mmole) in 15 ml of freshly distilled THF, cooled in an ice-water bath was added with stirring, dropwise a solution of 2.75 g of Part (9) bis-carbonate (6.3 mmole) in 10 ml of dry THF over a period of 15 minutes. After the addition was over, the reaction mixture was stirred at 0°-5° C. and finally at room temperature for 3 hours, whereupon it was placed in a cold-bath and an excess of hydride was carefully decomposed by slow addition of saturated sodium sulfate solution. Addition of saturated sodium sulfate solution was continued until all the inorganic salts were precipitated as a white granular solid. Solid magnesium sulfate was added to the reaction mixture and it was then filtered. The residue was thoroughly washed with THF and methylene chloride (1:1). The combined filtrate was concentrated under reduced pressure. The crude oily residue was chromatographed on a silica gel column and eluted with 50% ethyl acetate in hexane followed by ethyl acetate to obtain 1.85 g of desired title diol as a viscous oily residue (92.5% yield).

(12)
[2-(2-Tetrahydropyranyloxyethyl)-3-(3,3-dimethyl-2,4-dioxa-cyclopentyl)butane]-1,4-bismethanesulfonate To a solution of 960 μl of methanesulfonylchloride (12 mmole) in 10 ml of pyridine, cooled at −10° C. in a dry ice-acetone bath was added with stirring, a solution of 1.61 g of Part (11) diol (5.07 mmole) in 2 ml of pyridine and 5 ml of methylene chloride, dropwise over a period of 10 minutes. After the addition was over, the reaction mixture was allowed to warm to 0° C. and left at −0°–5° C. for 3 hours, whereupon it was diluted with ether and washed thoroughly with water and saturated copper sulfate solution to remove pyridine. The aqueous wash was extracted with ether (X3). The combined organic extract was washed with water, dried over anhydrous magnesium sulfate and concentrated under reduced pressure. The crude oily title bis-mesylate residue was further dried in vacuo and was then immediately used in the next reaction.

(13)
(3α,4α)-2-[Tetrahydro-4-(4,4-dimethyl-3,5-dioxa-cyclopentyl)-3-thienyl]ethanol, tetrahydropyranyloxy ether 2.4 g of recrystallized sodium sulfate nonahydrate (crystallized from hot ethanol) was added to 70 ml of dry dimethyl sulfoxide. Roughly 25 ml of dimethyl sulfoxide was removed by distillation under reduced pressure (bath temperature 90° C.). The reaction mixture was cooled to room temperature and the distillation head was replaced with a reflux condenser. A solution of the crude Part (12) bis-mesylate (∼5.07 mmole) in 5 ml of dimethyl sulfoxide and 5 ml of ether was added dropwise with stirring over a period of 5 minutes. The reaction mixture was now heated to 70° C. and maintained at that temperature for 3 hours, whereupon it was cooled, diluted with ether and washed thoroughly with water. The aqueous layer was re-extracted with ether (X2). The combined ether extract was dried over anhydrous magnesium sulfate and finally was concentrated under reduced pressure. The crude residue was chromatographed on a silica gel column and eluted with 5-15% ethyl acetate in hexane to obtain 1.36 g of desired title tetrahydrothiophane as an oil. (86% yield in two steps from diol).

(14)
(3α,4α)-2-[Tetrahydro-4-(4,4-dimethyl-3,5-dioxa-cyclopentyl)-3-thienyl]ethanol To a solution of 1.56 g of Part (13) tetrahydrothiophene-THP ether (4.93 mmole) in 10 ml of dry methanol and 10 ml of dry acetone was added with stirring 450 mg of dried and crushed Amberlyst-15 resin. The reaction mixture was stirred at room temperature under an argon atmosphere for 6 hours, whereupon it was diluted with ether and filtered through anhydrous magnesium sulfate. The filtrate was concentrated under reduced pressure and the crude oily residue was chromatographed on a silica gel column. Elution with 30% ethyl acetate in hexane, followed by 50% ethyl acetate in hexane and finally with ethyl acetate gave 1.06 g of desired title alcohol as a white crystalline solid (92.5% yield).

(15)
(3α,4α)-2-[Tetrahydro-4-(4,4-dimethyl-3,5-dioxa-cyclopentyl)-3-thienyl]-acetaldehyde To a solution of 400 μl of distilled oxalylchloride (5 mmole) in 10 ml of anhydrous methylene chloride, cooled at −78° C. in a dry ice-acetone bath was added with stirring, dropwise 800 μl of dry dimethylsulfoxide (11.2 mmole) over a period of 10 minutes. A rapid gas evolution occurred during its addition. After 20 minutes at −78° C., a solution of 712 mg of Part (14) alcohol (2.93 mmole) in 5 ml of methylene chloride was added dropwise at −78° C. over a period of 5 minutes. Additional stirring was continued for 30 minutes, whereupon 1.5 ml of distilled triethylamine was added at −78° C. After stirring at −78° C. for 20 minutes, the cooling bath was removed and the reaction mixture was warmed to 0° C., whereupon water was added to the reaction mixture. The reaction mixture was allowed to stand at room temperature for an additional 5 minutes, whereupon it was diluted with ether and washed thoroughly with water. The aqueous layer was extracted with ether (X3). The combined ether extract was dried over anhydrous magnesium sulfate and finally was concentrated under reduced pressure to obtain 727 mg of title aldehyde as an oily residue. This was used in the Wittig reaction without any additional purifications.

(16)
[3α(Z),4α]-7-[Tetrahydro-4-(4,4-dimethyl-3,5-dioxa-cyclopentyl)-3-thienyl]-5-heptenoic acid and

(17)
[3α(Z),4α]-7-[Tetrahydro-4-(4,4-dimethyl-3,5-dioxa-cyclopentyl)-3-thienyl]-5-heptenoic acid, methyl ester To a suspension of 2.66 g of carboxybutyltriphenylphosphonium bromide (6 mmole) in 20 ml of freshly distilled THF, cooled in an ice-water bath was added with stirring 7.2 ml of 1.4 M solution of K-t-amylate in toluene, dropwise. After the addition, the water bath was removed and the orange ylide suspension was stirred at room temperature for an additional 2 hours. It was again cooled in an ice-water bath and a solution of 727 mg of crude title (15) aldehyde (2.93 mmole) in 5 ml of dry THF was added dropwise. The reaction mixture was stirred at room temperature for an additional 1 hour, whereupon it was quenched by addition of glacial acetic acid. The reaction mixture was now diluted with ether and washed successively with water and saturated sodium bicarbonate solution (X3). The combined aqueous layer was extracted with ether (X2). The combined ether extract was dried over anhydrous magnesium sulfate and finally was concentrated under reduced pressure. The crude residue was triturated with ether and the precipitated phosphine oxide was filtered off. The filtrate was placed in a cold-water bath and etheral diazomethane solution was added with stirring until the yellow diazomethane color persisted for 15 minutes. Excess diazomethane was now removed by bubbling argon through the reaction mixture. It was now concentrated under reduced pressure and the crude residue was chromatographed on a silica gel column. Elution with 10-30% ethyl acetate in hexane gave 683 mg of desired title Wittig addition product (70% yield from alcohol) contaminated with ∼155 of the undesired E-olefin.

(18)

[3α(Z),4α]-7-[Tetrahydro-4-(1,2-dihydroxyethyl)-3-thienyl]-5-heptenoic acid, methyl ester To a solution of 683 mg of Part (17) acetonide (1.93 mmole) in 10 ml of anhydrous methanol was added with stirring a catalytic amount of p-toluene sulfonic acid (~5 mg). The reaction mixture was stirred at room temperature under an argon atmosphere for 24 hours, whereupon it was concentrated under reduced pressure and the crude residue was chromatographed on a silic gel column. Elution with 20% ethyl acetate in hexane gave 110 mg of unreacted acetonide. Further elution with 50% ethyl acetate in hexane and finally with ethyl acetate gave 427 mg of desired title diol (84% yield based on a recovered acetonide) as a colorless oil.

(19)

[3α(Z),4α]-7-[Tetrahydro-4-formyl-3-thienyl]-5-heptenoic acid, methyl ester

To 90 mg of Part (18) diol (0.31 mmole) in 2 ml of methanol at 25° C. was added a solution of 75 mg of sodium metaperiodate (0.34 mmole, 1.1 equiv.) in 1 ml of H$_2$O. After stirring at 25° C. for 1 hour, the reaction mixture was concentrated. The residue was diluted with 3 ml of H$_2$O, then extracted with three 10 ml portions of CH$_2$Cl$_2$. The combined organic layer was dried over anhydrous MgSO$_4$ and concentrated to give 80 mg of crude title aldehyde as a yellow oil. This was used immediately in the next reaction.

B.

[3α(Z),4α]-7-[4-Hydroxymethyltetrahydro-3-thienyl]-5-heptenoic acid, methyl ester To a solution of Part A aldehyde (ca. 1.05 mmole) in 3 ml of methanol at 0° C. was added 40 mg of sodium borohydride (1.05 mmole, 4 equiv.). After stirring at 0° C. for 15 minutes, the reaction mixture was poured into 15 ml of a saturated NH$_4$Cl solution. The aqueous solution was extracted with four 10 ml portions of ether. The combined ethereal extract was dried over anhydrous MgSO$_4$ and concentrated. The residue was purified on a silica gel column, with 35% ethyl acetate/hexanes as eluting solvents, to give 97 mg of title alcohol as an oil.

C.

[3α(Z),4α]-7-[4-[(Hexyloxy)methyl]-tetrahydro-3-thienyl]-5-heptenoic acid, hexyl ester A mixture of 50 mg of powdered potassium hydroxide (0.9 mmole, 10 equiv.) in 10 ml of dry xylene was distilled off until ca. 5 ml of solution remained. To the cooled remaining solution was added a solution of 20 mg of Part B alcohol (0.09 mmole) in 5 ml of xylene, and the resulting mixture was again distilled off to a volume of ca. 5 ml, then cooled to 25° C. A solution of 155 mg of hexylmesylate in 5 ml of dry xylene (0.9 mmole, 10 equiv.) was added and the reaction mixture was heated at reflux for 1 hour. The mixture was then cooled to 25° C. and diluted with 30 ml of ether. The ethereal solution was washed with three 10 ml portions of H$_2$O, dried over anhydrous MgSO$_4$, and concentrated. The residue was purified on a silica gel column, with 5% ethyl acetate in hexanes as eluting solvents, to give 40 mg of the desired title ether, contaminated with some unidentified product.

EXAMPLE 2

[3α(Z),4α]-7-[4-[(Hexyloxy)methyl]tetrahydro-3-thienyl]-5-heptenoic acid

To a solution of 84 mg of impure Example 1 ester (ca. 0.2 mmole) in 8 ml of dry THF, saturated with argon at 25° C. was added 2 ml of a 1N lithium hydroxide solution (2 mmole, 10 equiv.). After stirring at 25° C. for 3 days, the reaction mixture was concentrated. The residue was diluted with 5 ml of H$_2$O, acidified to pH 3 with a saturated solution of oxalic acid, and extracted with three 10 ml portions of ether. The combined ethereal extract was washed with two 10 ml portions of H$_2$O, dried over anhydrous MgSO$_4$, and concentrated. The residue was purified on a CC-7 silica gel column, with a gradient of ether/pentanes as eluting solvents, to give 37.3 mg of title acid as a light yellow oil.

TLC: Silica gel; 5% MeOH/CH$_2$Cl$_2$; R$_f$~0.6

Anal Calcd for C$_{18}$H$_{32}$O$_3$S: C, 65.81; H, 9.81; S, 9.76. Found: C, 65.67; H, 9.68; S, 9.48.

EXAMPLE 3

[3α(Z),4α]-7-[4-[(Hexylthio)methyl]tetrahydro-3-thienyl]-5-heptenoic acid, methyl ester

A.

[3a(Z),4a]-7-[4-Tetrahydro-4-tosyloxy-3-thienyl]heptenoic acid, methyl ester

To a solution of 50 mg of [3α(Z),4α]-7-[4-hydroxymethyltetrahydro-3-thienyl]-5-heptenoic acid, methyl ester (prepared as described in Example 1 Part B) (0.19 mmole) in 1 ml of pyridine at 25° C. was added 90 mg of p-toluenesulfonyl chloride (0.38 mmole, 2 equiv.). After stirring at 25° C. for 2 hours, the reaction mixture was diluted with 20 ml of ether. The ethereal solution was washed with three 5 ml portions of a saturated cupric sulfate solution, two 5 ml portions of H$_2$O, dried over anhydrous MgSO$_4$ and concentrated. The residue was purified on a silica gel column, with 5% ethyl acetate/hexanes (200 ml) and 25% ethyl acetate/hexanes (200 ml) as eluting solvents, to give 60 mg of title tosylate as a clear oil.

B.

[3α(Z),4α]-7-[4-[(Hexylthio)methyl]-tetrahydro-3-thienyl]-5-heptenoic acid, methyl ester To a solution of 18 mg of potassium t-butoxide (0.16 mmole, 1.1 equiv.) in 3 ml of dry THF at 25° C. under an argon atmosphere was added 90 mg of 1-hexanethiol (0.8 mmole, 5 equiv.). After stirring at 25° C. for 30 minutes, a solution of 60 mg of Part A tosylate (0.14 mmole) in 1 ml of THF was added and the reaction was heated at reflux . for 1 hour. The cooled reaction mixture was diluted with 30 ml of ether. The ethereal solution was washed with three 5 ml portions of a saturated NaHCO$_3$ solution and 5 ml of H$_2$O, then dried over anhydrous MgSO$_4$ and concentrated. The residue was purified on a silica gel column with 5% EtOAc/hexanes (100 ml) and 10% EtOAc/hexanes (100 ml) as eluting solvents, to give 51 mg of title thioether as a light yellow oil (contaminated with some hexane disulfide).

EXAMPLE 4

[3α(Z),4α]-7-[4-[(Hexylthio)methyl]tetrahydro-3-thienyl]-5-heptenoic acid

To a solution of 51 mg of crude Example 3 ester (ca. 0.14 mmole) in 4.2 ml of THF, saturated with argon, at 25° C. was added 1.4 ml of a 1N lithium hydroxide solution. After stirring at 25° C. for 20 hours, the reaction mixture was concentrated. The residue was diluted with 5 ml of H₂O, acidified to pH 3 with a saturated solution of oxalic acid, then extracted with three 10 ml portions of ether. The combined ethereal extract was washed with two 5 ml portions of H₂O, dried over anhydrous MgSO₄, and concentrated. The residue was purified on a CC-7 silica gel column, with a gradient of pentane/ether as eluting solvents, to give 36 mg of title compound as a light yellow oil.

TLC: Silica gel; 5% MeOH/CH₂Cl₂, $R_f \sim 0.55$ Anal Calcd for : $C_{18}H_{32}O_2S_2$: C, 62.74; H, 9.36; S, 18.61. Found: C, 62.41; H, 9.36; S, 18.43

EXAMPLE 5

3α(Z),4β]-7-[4-[(Hexyloxy)methyl]tetrahydro-3-thienyl]-5-heptenoic acid, hexyl ester

A.

[3α(Z),4β]-7-[Tetrahydro-4-formyl-3-thienyl]-5-heptenoic acid, methyl ester

To 140 mg of [3α(Z),4α]-7-[tetrahydro-4-formyl-3-thienyl]-5-heptenoic acid, methyl ester (prepared as described in Example 1, Part A (19) (0.58 mmole) in 2 ml of methanol is added 3.15 mg of sodium methoxide (58 μmole, 10%). After stirring at 25° C. for 2 hours, the reaction mixture is poured into 50 ml of a saturated aqueous ammonium chloride solution and extracted with three 10 ml portions of ether. The organic layer is washed with 10 ml of H₂O and dried over anhydrous MgSO₄ and concentrated to give 130 mg of title aldehyde as an oil. This was used without purification.

B.

[3α(Z),4β]-7-[Tetrahydro-4-hydroxymethyl-3-thienyl]-5-heptenoic acid, methyl ester To 43 mg of title A aldehyde (0.18 mmole) in 1 ml of methanol at 0° C. is added 6.8 mg of sodium borohydride (0.18 mmole, 4 eq.). After stirring at 0° C. for 10 minutes, the mixture is poured into 20 ml of a saturated NH₄Cl solution and extracted with three 10 ml portions of ether. The combined ethereal extract is dried over anhydrous MgSO₄ and concentrated to give 44 mg of title alcohol as an oil.

C.

[3α(Z),4β]-7-[4-[(Hexyloxy)methyl]-tetrahydro-3-thienyl]-5-heptenoic acid, hexyl ester To 100 mg of powdered potassium hydroxide (1.8 mmole, 10 eq.) in 20 ml of dry xylene is added a solution of 44 mg of title B alcohol (0.18 mmole) in 20 ml of dry xylene. The mixture is heated to reflux and ca. 20 ml of xylene is distilled off.

To the cooled remaining solution is added a solution of 309 mg of hexyl mesylate (1.8 mmole, 10 eq.) and the mixture is heated at reflux for 3 hours. The mixture is cooled to 25° C., diluted with 100 ml of ether and washed with two 20 ml portions of water. The organic layer is dried over anhydrous MgSO₄ and concentrated to give an oil which is purified on a silica gel column, eluting with 10% EtOAc/hexanes to yield 45 mg of title ester as a yellow oil.

EXAMPLE 6

[3α(Z),4β]-7-[4-[(Hexyloxy)methyl]tetrahydro-3-thienyl]-5-heptenoic acid

To 45 mg of Example 5 title C ester (0.14 mmole) in 6 ml of THF is added 1.6 ml of 1M lithium hydroxide solution. The mixture is stirred at 25° C. for 4 days and then concentrated. The residue is diluted with 10 ml of H₂O and acidified with a saturated oxalic acid solution to pH 3 and extracted with three 10 ml portions of ether. The combined ethereal extract is washed with two 10 ml portions of water, dried over anhydrous MgSO₄ and concentrated.

The residue is purified on a CC-7 silica gel column, eluting with a gradient of pentane/ether. The product is kept under high vacuum for 2 days to yield 28 mg of title compound as an oil.

EXAMPLE 7

[3α(Z),4β]-7-4-[(Phenyloxy)methyl]tetrahydro-3-thienyl]-5-heptenoic acid (a) Phenol (1 mmole) is added to a solution of 262 mg triphenylphosphine (1 mmole), diethylazodicarboxylate (1 mmole) and Example 1, Part B (1 mmole) alcohol in 25 ml of dry THF and is stirred at 23° C. for 48 hours. The reaction mixture is concentrated in vacuo and the residue is triturated with ether. Filtration, concentration of the filtrate under reduced pressure and finally chromatgraphy of the residue on a silica gel column gives [3α(Z),4α]-7-[4-[(phenyloxy)methyl]tetrahydro-3-thienyl]-5-heptenoic acid, methyl ester.

(b) Following the procedure set out in Example 6, the ester from part (a) is converted to the title acid.

EXAMPLE 8

[3α(Z),4α]-7-[4-[(Benzyloxy)methyl]tetrahydro-3-thienyl]-5-heptenoic acid

Following the procedure of Example 1 except substituting benzyl mesylate for hexyl mesylate, the title compound is obtained.

EXAMPLE 9

[3α(Z),4α-7-[4-[(Cyclohexyloxy)methyl]tetrahydro-3-thieny]5-heptenoic acid

Following the procedure of Example 1 except substituting cyclohexyl mesylate for hexyl mesylate, the title compound is obtained.

EXAMPLE 10

[3α(Z),4α]-7-[4-[(2-Pentenyloxy)methyl]tetrahydro-3-thienyl]3thienyl]-5-heptenoic acid Following the procedure of Example 1 except substituting 2-pentenyl-1-mesylate for hexyl mesylate, the title compound is obtained.

EXAMPLE 11

[3α(Z),4α]-7-[4-[(Cyclopentylmethyloxy)methyl]-tetrahydro-3-thienyl]-5-heptenoic acid Following the procedure of Example 1 except substituting cyclopentylmethyl mesylate for hexyl mesylate, the title compound is obtained.

EXAMPLE 12

[3α(Z),4β]-7-[4-[(Heptyloxy)methyl]tetrahydro-3-thienyl-5-heptenoic acid

Following the procedure of Examples 2 and 3 except substituting heptyl mesylate for hexyl mesylate, the title compound is obtained.

EXAMPLE 13

[3α(Z),4β]-7-[4-[(Phenethyloxy)methyl]tetrahydro-3-thienyl]-5-heptenoic acid

Following the procedure of Examples 5 and 6 except substituting phenethyl mesylate for hexyl mesylate, the title compound is obtained.

EXAMPLE 14

[3α(Z),4β]-7-[4-[(Cyclopentyloxy)methyl]-tetrahydro-3-thienyl]-5-heptenoic acid

Following the procedure of Examples 5 and 6 except substituting cyclopentyl mesylate for hexyl mesylate, the title compound is obtained.

EXAMPLE 15

[3α(Z),4β]-7-[4-[(Cyclohexyloxy)methyl]tetrahydro-3-thienyl]-5-heptenoic acid

Following the procedure of Examples 5 and 6 except substituting cyclohexyl mesylate for hexyl mesylate, the title compound is obtained.

EXAMPLE 16

[3α(Z),4β]-7-[4-[(3-Butenyloxy)methyl]tetrahydro-3-thienyl]-5-heptenoic acid

Following the procedure of Examples 5 and 6 except substituting 3-butenyl mesylate for hexyl mesylate, the title compound is obtained.

EXAMPLE 17

[3α(Z),4α]-7-[4-[(2-Hexenylthio)methyl]tetrahydro-3-thienyl]-5-heptenoic acid

Following the procedure of Examples 3 and 4 except substituting 2-hexenyl-1-thiol for hexanethiol, the title compound is obtained.

EXAMPLE 18

[3α(Z),4α]-7-[4-[(Propylthio)methyl]tetrahydro-3-thienyl]-5-heptenoic acid

Following the procedure of Examples 3 and 4 except substituting propylthiol for hexanethiol, the title compound is obtained.

EXAMPLE 19

[3α(Z),4α]-7-[4-[(Cycloheptylthio)methyl]tetrahydro-3-thienyl]-5-heptenoic acid

Following the procedure of Examples 3 and 4 except substituting cycloheptylmercaptan for hexanethiol, the title compound is obtained.

EXAMPLE 20

[3α(Z),4α]-7-[4-[(Benzylthio)methyl]tetrahydro-3-thienyl-5-heptenoic acid

Following the procedure of Examples 3 and 4 except substituting benzylmercaptan for hexanethiol, the title compound is obtained.

EXAMPLE 21

[3α(Z),4α]-7-[4-[(Phenylthio)methyl]tetrahydro-3-thienyl]-5-heptenoic acid

Following the procedure of Examples 3 and 4 except substituting phenylmercaptan for hexanethiol, the title compound is obtained.

EXAMPLE 22

(3α,4α)-7-[4-[(Hexyloxy)methyl]tetrahydro-3-thienyl]-heptanoic acid

A.

[3α,4α(1S)]-7-[Tetrahydro-4[(1-hydroxymethyl)methyl]-3-furanyl]-heptanoic acid, methyl ester A mixture of 600 mg of Example 1 Part A (18) diol, 100 mg of a 10% palladium over carbon in 80 ml of EtOAc and 4 ml of glacial acetic acid is shaken in a Parr bottle under 50 lb. of hydrogen pressure at 25° C. for 24 hours. The mixture is then filtered through a bed of Celite. The filtrate is concentrated to give title A diol.

B. (3α,4α)-7-[Tetrahydro-(1-formyl)-3-thienyl]heptanoic acid, methyl ester

To a solution of 600 mg of title A diol (1.9 mmole) in 5 ml methanol at 25° C. is added a solution of 490 mg of Na m-periodate in 1 ml $H_2O$. The mixture is stirred at 25° C. for 30 minutes, then extracted with 3-10 ml portions of $CH_2Cl_2$. The organic layer is dried over anhydrous $MgSO_4$ and concentrated to give title aldehyde

C.

[3α,4α]-7-[4-[(Hexyloxy)methyl]-tetrahydro-3-thienyl]-heptanoic acid

Following the procedure of Example 1 Parts B and C except substituting the above Part B aldehyde for the Example 1 Part A (19) aldehyde, the title acid is obtained.

EXAMPLE 23

(3α,4α)-7-[4-[(Benzyloxy)methyl]tetrahydro-3-thienyl]-heptanoic acid

Following the procedure of Example 22 except substituting benzyl mesylate for hexyl mesylate, the title compound is obtained.

EXAMPLE 24

(3α,4α)-7-[4-[(Phenyloxy)methyl]tetrahydro-3-thienyl]-heptanoic acid

A. (3α,4α)-7-[4-(Hydroxymethyl)tetrahydro-3-thienyl]heptanoic acid, methyl ester Following the procedure of Example 1 Part B except substituting Example 22, Part B aldehyde for Example 1 Part A aldehyde, the title alcohol is obtained.

B.
(3α,4α)-7-[4-[(Phenyloxy)methyl]tetrahydro-3-furanyl]-heptanoic acid

Following the procedure of Example 7 except substituting the above title A alcohol for Example 1 Part B alcohol, the title compound is obtained.

EXAMPLE 25

(3α,4α)--7-[4-[(Cyclohexyloxy)methyl]tetrahydro-3-thienyl]heptanoic acid

Following the procedure of Example 22 except substituting cyclohexyl mesylate for hexyl mesylate, the title compound is obtained.

EXAMPLE 26

(3α,4α)-7-[4-[(2-Butenyloxy)methyl]tetrahydro-3-thienyl]heptanoic acid

Following the procedure of Example 22 except substituting 2-butenyl-1-mesylate for hexyl mesylate, the title compound is obtained.

EXAMPLE 27

(3α,4β)-7-[4-[(Benzyloxy)methyl]tetrahydro-3-thienyl]heptanoic acid

Following the procedure of Example 22 except substituting the Example 5 Part A aldehyde for the Example 1 Part A (19) aldehyde and substituting benzyl mesylate for hexyl mesylate, the title compound is obtained.

EXAMPLE 28

(3α,4β)-7-[4-[(Phenyloxy)methyl]tetrahydro-3-thienyl]heptanoic acid

A. (3α,4β)-7-[4-Formyl-tetrahydro-3-furanyl]heptanoic acid, methyl ester

Following the procedure of Example 5 Part B except substituting Example 22 Part B aldehyde for Example 5 Part A aldehyde, the title aldehyde is obtained.

B. (3α,4β)-7-[4-[(Phenyloxy)methyl]-tetrahydro-3-thienyl]heptanoic acid

Following the procedure of Example 24 except substituting the above Part A aldehyde for Example 21 Part B aldehyde in Example 24 Part A, the title acid is obtained.

EXAMPLE 29

(3α,4β)-7-[4-[(Cyclopropyloxy)methyl]-tetrahydro-3-thienyl]heptanoic acid

Following the procedure of Example 22 except substituting the Example 5 Part A aldehyde for the Example 1 Part A (19) aldehyde and substituting cyclopropyl mesylate for hexyl mesylate, the title compound is obtained.

EXAMPLE 30

(3α,4β)-7-[4-[(Cyclopentylethyloxy)methyl]-tetrahydro-3-thienyl]heptanoic acid

Following the procedure of Example 22 except substituting the Example 5 Part A aldehyde for the Example 1 Part A (19) aldehyde and substituting cyclopentylethyl mesylate for hexyl mesylate, the title compound is obtained.

EXAMPLE 31

(3α,4β)-7-[4-[(3-Hexenyloxy)methyl]tetrahydro-3-thienyl]heptanoic acid

Following the procedure of Example 22 except substituting the Example 5 Part A aldehyde for the Example 1 Part A (19) aldehyde and substituting 3-hexenyl-1-mesylate for hexyl mesylate, the title compound is obtained.

EXAMPLE 32

(3α,4α)-7-4-[(Octylthio)methyl]tetrahydro-(3 3-thienyl]heptanoic acid

Following the procedure of Example 22 Parts A and B and Examples 3 and 4 except substituting the Example 22 Part B aldehyde in Examples 3 and 4 for the Example 1 Parts A (16) aldehyde and substituting octylthiol for hexanethiol, the title compound is obtained.

EXAMPLE 33

(3α,4α)-7-[4-[(Phenylthio)methyl]tetrahydro-3-thienyl]heptanoic acid

Following the procedure of Example 22 Parts A and B and Examples 3 and 4, substituting the Example 22 Part B aldehyde for the Example 1 Part A (19) aldehyde in Examples 3 and 4 and substituting phenylmercaptan for hexanethiol, the title compound is obtained.

EXAMPLE 34

(3α,4α)-7-[4-[(Benzylthio)methyl]tetrahydro-3-thienyl]heptanoic acid

Following the procedure of Example 22 Parts A and B and Examples 3 and 4, substituting the Example 22 Part B aldehyde for the Example 1 Part A (19) aldehyde in Examples 3 and 4 and substituting benzylmercaptan for hexanethiol, the title compound is obtained.

EXAMPLE 35

(3α,4α)-7-[4-[(Cyclopentylthio)methyl]-tetrahydro-3-thienyl]heptanoic acid

Following the procedure of Example 22 Parts A and B and Examples 3 and 4, substituting the Example 22 Part B aldehyde for the Example 1 Part A (19) aldehyde in Examples 3 and 4 and substituting cyclopentylmercaptan for hexanethiol, the title compound is obtained.

EXAMPLE 36

(3α,4α)-7-[4-[(Cyclohexylmethylthio)methyl]-tetrahydro-3-thienyl]heptanoic acid

Following the procedure of Example 22 Parts A and B and Examples 3 and 4, substituting the Example 22 Part B aldehyde for the Example 1 Part A (19) aldehyde in Examples 3 and 4 and substituting cyclohexylmethylmercaptan for hexanethiol, the title compound is obtained.

EXAMPLE 37

(3α,4α)-7-[4-[(2-Octenylthio)methyl]tetrahydro-3-thienyl]heptanoic acid

Following the procedure of Example 22 Parts A and B and Examples 3 and 4, substituting the Example 21 Part B aldehyde for the Example 1 Part A (19) aldehyde in Examples 3 and 4 and substituting 2-octenyl-1-thiol for hexanethiol, the title compound is obtained.

EXAMPLE 38

[3α(Z),4α]-7-[4-[2-(Hexyloxy)ethyl]tetrahydro-3-thienyl]-5-heptenoic acid

A.
[3α(Z),4α]-7-[4-[2-(2-Oxo)ethyl]-tetrahydro-3-thienyl]-5-heptenoic acid, methyl ester Into a dry 100 ml round bottom 3-necked flask containing a stir bar is added dried 3.27 g (9.54 mmoles) methoxymethyltriphenylphosphonium chloride ((C$_6$H$_5$)$_3$P$^{30}$-CH$_2$OCH$_3$Cl$^{31}$) $^{and}$ 30 ml distilled toluene (stored over molecular sieves). The resulting suspension is stirred in an ice-bath, under argon, until cold and then a 1.4 M solution of 5.73 ml (8.01 mmol) of potassium t-amylate in toluene is added dropwise. A bright red solution formed which is stirred at 0° C. for an additional 35 minutes. Thereafter, a solution of 900 mg (3.75 mmol) [3α(Z),4α]-7-(4-formyl)tetrahydro-3-thienyl]-5-heptenoic acid, methyl ester (prepared as described in Example 1 Part A (19)) in 10 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated NH$_4$Cl, and extracted with ether (4 × 200 ml). The combined ether phases are washed with NaCl saturated solution, and dried (MgSO$_4$) and concentrated to yield an oil in a white crystalline solid (phosphine oxide). The white solid is triturated with EtOAc and the mother liquor is purified by chromatography on an LPS-1 silica column to obtain the enol-ether. The enol-ether is dissolved in 20 ml of THF and is then treated with 10 ml of a 20% aqueous trifluoroacetic acid solution. After 1 hour, trifluoroacetic acid is quenched by addition of solid NaHCO$_3$. The reaction mixture is extracted several times with methylene chloride. The methylene chloride extract is dried over anhydrous magnesium sulfate and concentrated under reduced pressure. The crude residue is chromtographed on a silica gel column to obtain the desired title A aldehyde.

B.
[3α(Z),4α]-7-[[4-(2-Hydroxyethyl)]-tetrahydro-3-thienyl]-5-heptenoic acid, methyl ester The aldehyde (762 mg, 3 mmol) from part A in methanol (50 ml) is treated with NaBH$_4$ (0.11 g, 3 mmol) in an argon atmosphere at 0° C. After stirring at 0° C. for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound. cl C. [3α(Z),4α]-7-[[4-[2-(Hexyloxy)ethyl]- tetrahydro-3-thienyl]-5-heptenoic acid Following the procedure of Example 1, Part C and Example 5 except substituting the above part B alcohol for the Example 1 Part B alcohol used in Example 1 Part C, the title compound is obtained.

EXAMPLE 39

[3α(Z),4α]-7-[4-[2-(Hexylthio)ethyl]tetrahydro-3-thienyl]-5-heptenoic acid

Following the procedure of Examples 3 and 4 except substituting [3α(Z),4α]-7-[4-[2-(2-oxo)-ethyl]tetrahydro-3-thienyl]-5-heptenoic acid, methyl ester (prepared as described in Example 38 Part A) for the Example 1 Part B alcohol used in Example 3, Part A, the title compound is obtained.

EXAMPLE 40

[3α(Z),4α]-7-[4-[2-(Benzyloxy)ethyl]tetrahydro-3-thienyl]-5-heptenoic acid

Following the procedure of Example 38 except substituting benzyl mesylate for hexyl mesylate, the title compound is obtained.

EXAMPLE 41

[3α(Z),4α]-7-4-[2-(Phenyloxy)ethyl]tetrahydro-3-thienyl]-5-heptenoic acid

Following the procedure of Example 7 except substituting Example 38 Part B alcohol for Example 1 Part B alcohol, the title acid is obtained.

EXAMPLE 42

[3α(Z),4α]-7-[4-[2-(1-Butenyloxy)ethyl]tetrahydro-3-thienyl]-5-heptenoic acid

Following the procedure of Example 38 except substituting 1-butenyl mesylate for hexyl mesylate, the title compound is obtained.

EXAMPLE 43

[3α(Z),4α]-7-[4-[2-(Cyclohexyloxy)ethyl]-tetrahydro-3-thienyl]-5-heptenoic acid

Following the procedure of Example 38 except substituting cyclohexyl mesylate for hexyl mesylate, the title compound is obtained.

EXAMPLE 44

[3α(Z),4α]-7-[4-[2-(Propyloxy)ethyl]tetrahydro-3-thienyl]-5-heptenoic acid

Following the procedure of Example 38 except substituting n-propyl mesylate for hexyl mesylate, the title compound is obtained.

EXAMPLE 45

[3α(Z),4α]-7-[4-[2-(Cyclopentylmethyloxy)ethyl-tetrahydro-3-thienyl]-5-heptenoic acid Following the procedure of Example 38 except substituting cyclopentylmethyl mesylate for hexyl mesylate, the title compound is obtained.

EXAMPLE 46

[3α(Z),4α]-7-[4-[2-(Pentylthio)ethyl]tetrahydro-3-thienyl]-5-heptenoic acid

Following the procedure of Example 39 except substituting 1-pentanethiol for 1-hexanethiol, the title compound is obtained.

EXAMPLE 47

[3α(Z),4α]-7-[4-[2-(Benzylthio)ethyl]tetrahydro-3-thienyl]-5-heptenoic acid

Following the procedure of Example 39 except substituting benzylmercaptan for 1-hexanethiol, the title compound is obtained.

EXAMPLE 48

[3α(Z),4α]-7-[4-[2-(Phenylthio)ethyl]tetrahydro-3-thienyl]-5-heptenoic acid

Following the procedure of Example 39 except substituting phenylmercaptan for 1-hexanethiol, the title compound is obtained.

EXAMPLE 49

[3α(Z),4α]-7-[4-[2-(Cyclohexylthio)ethyl]tetrahydro-3-thienyl]-5-heptenoic acid

Following the procedure of Example 39 except substituting cyclohexylmercaptan for 1-hexanethiol, the title compound is obtained.

EXAMPLE 50

[3α(Z),4α]-7-[4-[2-(Cyclohexylmethylthio)ethyl]tetrahydro-3-thienyl]-5-heptenoic acid Following the procedure of Example 39 except substituting cyclohexylmethylmercaptan for 1-hexanethiol, the title compound is obtained.

EXAMPLE 51

[3α(Z),4α]-7-[4-[2-(1-Propenylthio)ethyl]tetrahydro-3-thienyl]-5-heptenoic acid

Following the procedure of Example 39 except substituting 1-(1-propenyl)thiol for 1-hexanethiol, the title compound is obtained.

EXAMPLE 52

(3α,4α)-7-[4-[2-(Hexyloxy)ethyl]tetrahydro-3-thienyl]-heptanoic acid

Following the procedure of Example 38 except substituting the Example 22 Part B aldehyde for the Example 1 Part A (19) aldehyde used in Example 38 Part A, the title compound is obtained.

EXAMPLE 53

(3α,4α)-7-[4-[2-(Cyclopentylethyloxy)ethyl]tetrahydro-3-thienylheptanoic acid

Following the procedure of Example 38 except substituting the Example 22 Part B aldehyde for the Example 1 Part A (19) aldehyde used in Example 38 Part A and substituting cyclopentylethyl mesylate for hexyl mesylate, the title compound is obtained.

EXAMPLE 54

(3α,4α)-7-[4-[2-(Benzyloxy)ethytetrahydro 3-thienyl]heptanoic acid

Following the procedure of Example 38 except substituting the Example 22 Part B aldehyde for the Example 1 Part A (19) aldehyde used in Example 38 Part A and substituting benzyl mesylate for hexyl mesylate, the title compound is obtained.

EXAMPLE 55

(3α,4α)-7-[4-[2-(Phenyloxy)ethyl]tetrahydro-3-thienyl]-5-heptanoic acid

Following the procedure of Examples 38 and 7 except substituting the Example 22 Part B aldehyde for the Example 1 Part A (19) aldehyde used in Example 38 Part A and substituting the resulting (3α,4α)-7-[4-2-(hydroxyethyl)]tetrahydro-3-thienyl]heptanoic acid, methyl ester for Example 1 Part B alcohol in Example 7 Part (a), the title acid is obtained.

EXAMPLE 56

(3α,4α)-7-[4-[2-(Cyclopentyloxy)ethyl]tetrahydro-3-thienyl]heptanoic acid

Following the procedure of Example 38 except substituting the Example 22 Part B aldehyde for the Example 1 Part A (19) aldehyde used in Example 38 Part A and substituting cyclopentyl mesylate for hexyl mesylate, the title compound is obtained.

EXAMPLE 57

(3α,4α)-7-[4-[2-(3-Hexenyloxy)ethyl]tetrahydro-3-thienyl]heptanoic acid

Following the procedure of Example 38 except substituting the Example 22 Part B aldehyde for the Example 1 Part A (19) aldehyde used in Example 38 Part A and substituting 3-hexenyl mesylate for hexyl mesylate, the title compound is obtained.

EXAMPLE 58

(3α,4α)-7-[4-[2-(Cyclopropylmethylthio)ethyl]tetrahydro-3-thienyl]heptanoic acid Following the procedure of Example 39 except substituting the Example 22 Part B aldehyde for the Example 38 Part A aldehyde and substituting cyclopropylmethyl mercaptan for 1-hexanethiol, the title compound is obtained.

EXAMPLE 59

(3α,4α)-7-[4-[2-(Benzylthio)ethyl]tetrahydro-3-thienyl]-heptanoic acid

Following the procedure of Example 39 except substituting the Example 22 Part B aldehyde for the Example 38 Part A aldehyde and substituting benzylmercaptan for 1-hexanethiol, the title compound is obtained.

EXAMPLE 60

(3α,4α)-7-4-2-(Phenylthio)ethyl]tetrahydro-3-thienyl]-heptanoic acid

Following the procedure of Example 39 except substituting the Example 22 Part B aldehyde for the Example 38 Part A aldehyde and substituting phenylmercaptan for 1-hexanethiol, the title compound is obtained.

EXAMPLE 61

(3α,4α)-7-[4-[2-(Cyclohexylthio)ethyl]tetrahydro-3-thienyl]heptanoic acid

Following the procedure of Example 39 except substituting the Example 22 Part B aldehyde for the Example 38 Part A aldehyde and substituting cyclohexylmercaptan for 1-hexanethiol, the title compound is obtained.

EXAMPLE 62

(3α,4α)-7-[4-[2-(2-Heptenylthio)ethyl]tetrahydro-3-thienyl]heptanoic acid

Following the procedure of Example 39 except substituting the Example 22 Part B aldehyde for the Example 38 Part A aldehyde and substituting 1-(2-heptenyl)-thiol for 1-hexanethiol, the title compound is obtained.

EXAMPLE 63
[3α(Z),4α]-7-[4-[4-(Hexyloxy)butyl]tetrahydro-3-thienyl-5-heptenoic acid

A.
[3α(Z),4α]-7-[4-[3-(3-Oxo)propyl]tetrahydro-3-thienyl]-5-heptenoic acid, methyl ester Following the procedure of Example 38 Part A except substituting [3α(Z),4α]-7-[4-[2-(2-oxo)ethyl]tetrahydro-3-thienyl]-5-heptenoic acid, methyl ester for [3α(Z),4α]-7-[(4-formyl)tetrahydro-3-thienyl]-5-heptenoic acid, methyl ester, the title A compound is obtained.

B.
[3α(Z),4α]-7-[4-(4-Oxo)butyl]tetrahydro-3-thienyl]-5-heptenoic acid, methyl ester Following the procedure of Example 38 Part A except substituting the aldehyde from Part A above for [3α(Z),4α]-7-[4-[2-(2-oxo)ethyl]tetrahydro-3-thienyl]-5-heptenoic acid, methyl ester, the title B aldehyde is obtained.

C.
[3α(Z),4α]-7-[4-(4-Hydroxybutyl)]tetrahydro-3-thienyl]-5-heptenoic acid, methyl ester Following the procedure of Example 38 Part B except substituting the title B aldehyde for

[3α(Z),4α]-7-[4-[2-(2-oxo)ethyl]tetrahydro-3-thienyl]-5-heptenoic acid, methyl ester, the title C alcohol is obtained.

D.
[3α(Z),4α]-7-[4-[4-(Hexyloxy)butyltetrahydro-3-thienyl]-5-heptenoic acid Following the procedure of Example 1 except substituting the above part C alcohol for the alcohol used in Example 1 Part C, the title compound is obtained.

EXAMPLE 64
[3α(Z), 4α]-7-[4-[4-(Benzyloxy)butyl]tetrahydro-3-thienyl]-5-heptenoic acid Following the procedure of Examples 63 and except substituting the Example 63 Part C alcohol for the Example 38 Part A alcohol and substituting benzyl mesylate for hexyl mesylate, the title compound is obtained.

EXAMPLE 65
[3α(Z),4α]-7-[4-[4-(Cyclohexylthio)butyl]tetrahydro-3-thienyl]-5-heptenoic acid Following the procedure of Examples 63, 38 and 39 except substituting the Example 63 Part C alcohol for the Example 38 Part B alcohol and substituting cyclohexylmercaptan for 1-hexanethiol, the title compound is obtained.

EXAMPLE 66
[3α(Z),4α-7-[4-[(Hexylsulfinyl)methyl]tetrahydro-3-thienyl]-5-heptenoic acid and [3α(Z),4α]-7-[4-(Hexylsulfonyl)methyl]tetrahydro-3-thienyl]-5-heptenoic acid To a solution of 562 mg (1.72 mmol) of [3α(Z),4α]-7-[4-[(hexylthio)methyl]tetrahydro-3-thienyl]-5-heptenoic acid, methyl ester (prepared as described in Example 4) in 6.78 ml of methanol at 0° C. is added dropwise over 4 minutes 8.37 ml of 0.5 M aqueous sodium periodate solution. Tetrahydrofuran (2 ml) is then added and the resulting reaction mixture is stirred at room temperature for 15 hours. A white precipitate is removed by filtration and washed with ether (3×50 ml). The filtrate is washed with 60 ml of saturated aqueous $NaHCO_3$ solution and dried over anhydrous magnesium sulfate. Concentration in vacuo affords 539 mg of an oily crude product. This is chromatographed on 54.16 g of silica gel 60 using 0.5–1.0% $CH_3OH$ to give the title compounds.

EXAMPLE 67
[3α(Z),4α]-7-[4-[(Hexylsulfonyl)methyl]tetrahydro-3-thienyl]-5-heptenoic acid To a stirred solution of 143 mg (0.4 mmol) of the Example 66 sulfonyl compound in 20.3 ml of THF and 3.09 ml of $H_2O$ under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 30 ml of saturated NaCl solution. The resulting solution is saturated with solid NaCl and extracted with EtOAc (4×50 ml). The combined EtOAc extracts are dried ($MgSO_4$), filtered and concentrated in vacuo to give 140 mg of crude acid which is purified by flash chromatography.

EXAMPLE 68
[3α(Z),4α]-7-[4-[(Hexylsulfinyl)methyl]tetrahydro-3-thienyl]-5-heptenoic acid To a stirred solution of 120 mg (0.35 mmol) of Example 66 ester and sulfinyl ester in 27.0 ml of THF and 4.11 ml of $H_2O$ under argon is added 5.19 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 50 ml of saturated NaCl solution. The resulting solution is saturated with solid NaCl and extracted with EtOAc (4×100 ml). The combined EtOAc extracts are dried ($MgSO_4$), filtered and concentrated in vacuo to give crude acid which is purified by flash chromatography.

EXAMPLE 69
[3α(Z),4α]-7-[4-[2-(Hexyloxymethyl)]tetrahydro-3-thienyl]-2,5-heptadienoic acid

A. [3α(Z),4α]-7-[4-[2-(Hexyloxymethyl)]-tetrahydro-3-thienyl]-2-selenophenyl-5-heptenoic acid, methyl ester To a solution of 308 μl of diisopropylamine (2.2 mmole) in 5 ml of dry THF, cooled at -78° C., is added dropwise 1.25 ml of a 1.6 M solution of n-butyllithium in hexane. After 30 minutes at −78° C., a solution of 356 mg of [3α(Z),4α]-7-[4-[(hexyloxy)methyl]tetrahydro-3-thienyl]-5-heptenoic acid, hexyl ester, prepared as described in Example 5, (1 mmole) in 2 ml of dry THF is added dropwise. The reaction mixture is stirred for 30 minutes, whereupon a solution of 625 mg of diphenyldiselenide (2 mmole) in 2 ml of dry THF is added. The yellow color of diselenide disappears immediately upon its addition, initially. The yellow solution is stirred at −78° C. for 30 minutes, whereupon the cooling bath was removed. The reaction mixture is then quenched by addition of aqueous ammonium chloride solution. It is then diluted with water and the organic layer is separated. The aqueous layer is extracted with ether. The combined organic extract is dried over anhydrous magnesium sulfate and concentrated in vacuo. Purification by chromatography on a silica gel column and eluting with 5–25% ethyl acetate in hexane gives 600 mg of title α-selenophenyl ester (90% yield).

B.

[3α(Z),4β]-7-[4-[2-(Hexyloxymethyl)]-tetrahydro-3-thienyl-2-selenophenyl- 5-heptenoic acid A solution of 600 mg of title A α-selenophenyl esters in 10 ml of distilled THF is treated with 5 ml of a 1 N aqueous lithium hydroxide solution. After stirring at room temperature for 2 days, the reaction mixture is acidified with 1 N aqueous hydrochloric acid solution and extracted with methylene chloride. The methylene chloride extract is dried over anhydrous magnesium sulfate and concentrated in vacuo to yield 560 mg of title acid.

C.

[3α(Z),4β]-7-[4-[2-(Hexyloxymethyl)]tetrahydro-3-thienyl]-2,5-heptadienoic acid

A solution of 560 mg of title B acid (0.86 mmole) in 10 ml of distilled THF is treated with 500 ml of a 30% aqueous hydrogen peroxide solution at 0–5° C. After a few minutes, the cooling bath is removed and the reaction mixture is stirred at room temperature for 1 hour. It is then diluted with methylene chloride and washed thoroughly with water. The organic layer is dried over anhydrous MgSO$_4$ and concentrated under reduced pressure. The crude residue is chromatographed on a CC-7 silica gel column and eluted with 20–60% ethyl acetate in hexane to obtain the title α,β-unsaturated acid.

EXAMPLE 70

[3α(Z),4α]-7-[4-[2-(Hexylthio)methyl]tetrahydro-3-thienyl]-2,5-heptadienoic acid Following the procedure of Example 69 except substituting the Example 3 compound for the Example 5 compound in Example 69 Part A, the title compound is obtained.

EXAMPLE 71

[3α(Z), 4α]-7-[4-[2-(Phenyloxy)methyl]tetrahydro-b 3-thienyl]-2,5-heptadienoic acid Following the procedure of Example 69 except substituting the ester compound prepared in Example 7 for the Example 5 compound in Example 69, Part A, the title compound is obtained.

EXAMPLE 72

[3α(Z),4α]-7-[4-[2-(Benzyloxy)methyl]tetrahydro-3-thienyl]-2,5-heptadienoic acid Following the procedure of Example 69 except substituting the ester compound prepared in Example 8 for the Example 5 compound in Example 69 Part A, the title compound is obtained.

EXAMPLE 73

[3α(Z),4α]-7-[4-[(2-Pentenyloxy)methyl]tetrahydro3-thienyl]-2,5-heptadienoic acid Following the procedure of Example 69 except substituting the ester compound prepared in Example 10 for the Example 5 compound in Example 69 Part A, the title compound is obtained.

EXAMPLE 74

[3α(Z),4α]-7-[4-[(Heptyloxy)methyl)]tetrahydro-3-thienyl]-2,5-heptadienoic acid

Following the procedure of Example 69 except substituting the ester compound prepared in Example 12 for the Example 5 compound in Example 69 Part A, the title compound is obtained.

EXAMPLE 75

[3α(Z),4α]-7-[4-[(Cyclopentyloxy)methyl]tetrahydro-3-thienyl]-2,5-heptadienoic acid Following the procedure of Example 69 except substituting the ester compound prepared in Example 14 for the Example 5 compound in Example 24 Part A, the title compound is obtained.

EXAMPLE 76

[3α(Z),4β]-7-[4-[(Cyclohexyloxy)methyl]tetrahydro-3-thienyl]-2,5-heptadienoic acid Following the procedure of Example 69 except substituting the ester compound prepared in Example 15 for the Example 5 compound in Example 69 Part A, the title compound is obtained.

EXAMPLE 77

[3α(Z),4β]-7-[4-[(3-Butenyloxy)methyl]tetrahydro-thienyl]-2,5-heptadienoic acid

Following the procedure of Example 69 except substituting the ester compound prepared in Example 16 for the Example 5 compound in Example 68 Part A, the title compound is obtained.

EXAMPLE 78

[3α(Z),4α]-7-[4-[(2-Hexenylthio)methyl]tetrahydro-3-thienyl]-2,5-heptadienoic acid Following the procedure of Example 69 except substituting the ester compound prepared in Example 17 for the Example 5 compound in Example 69 Part A, the title compound is obtained.

EXAMPLE 79

(3α,4α)-7-[4-[(Hexyloxy)methyl)]tetrahydro-3-thienyl]-2,5-heptadienoic acid

Following the procedure of Example 69 except substituting the ester compound prepared in Example 22 for the Example 5 compound in Example 69 Part A, the title compound is obtained.

EXAMPLE 80

(3α,4α)-7-[4-[(Octylthio)methyl]tetrahydro-3-thienyl]-2-heptenoic acid

Following the procedure of Example 69 except substituting the ester compound prepared in Example 32 for the Example 5 compound in Example 69 Part A, the title compound is obtained.

EXAMPLE 81

[3α(Z),4α]-7-[4-[2-(Hexyloxy)ethyl]tetrahydro-3-thienyl]-2,5-heptadienoic acid

Following the procedure of Example 69 except substituting the ester compound prepared in Example 38 for the Example 5 compound in Example 69 Part A, the title compound is obtained.

EXAMPLE 82

[3α(Z),4α]-7-[4-[2-(Hexylthio)ethyl]tetrahydro-3-thienyl]-2,5-heptadienoic acid

Following the procedure of Example 69 except substituting the ester compound prepared in Example 39 for the Example 5 compound in Example 69 Part A, the title compound is obtained.

EXAMPLE 83

(3α,4α)-7-[4-[2-(Hexyloxy)ethyl]tetrahydro-3-thienyl]-2-heptenoic acid

Following the procedure of Example 69 except substituting the ester compound prepared in Example 52 for the Example 1 compound in Example 69 Part A, the title compound is obtained.

EXAMPLE 84

(3α,4α)-7-[4-[2-(Cyclohexylthio)ethyl]tetrahydro-3-thienyl]-2-heptenoic acid

Following the procedure of Example 69 except substituting the ester compound prepared in Example 61 for the Example 1 compound in Example 69 Part A, the title compound is obtained.

EXAMPLES 85 to 94

Following the procedure as outlined in the specification and described in the working Examples, the following additional compounds may be prepared.

$$\underset{S}{\diagup\!\!\diagdown}\!\!\begin{array}{c}CH_2-A-(CH_2)_m-B-COOH\\(CH_2)_n-X-R^1\end{array}$$

| Ex. No. | A | m | B | $(CH_2)_n$ | $R^1$ | X |
|---|---|---|---|---|---|---|
| 85. | CH=CH | 1 | CH=CH | $CH_2$ | $CH_3CH=CH$ | S |
| 86. | $(CH_2)_2$ | 2 | CH=CH | $(CH_2)_2$ | $CH_3CH_2CH=CHCH_2-$ | O |
| 87. | — | 3 | CH=CH | $(CH_2)_3$ | cyclopentyl | $\underset{\overset{\|}{O}}{\overset{\|}{S}}$ |
| 88. | CH=CH | 4 | — | $-CHCH_2-$<br>$CH_3$ | cyclohexyl-$CH_2$ | $\underset{\overset{\|}{O}}{\overset{\overset{O}{\|}}{S}}$ |
| 89. | $(CH_2)_2$ | 5 | CH=CH | $(CH_2)_4$ | $C_6H_5$ | S |
| 90. | CH=CH | 6 | — | $(CH_2)_5$ | $C_6H_5(CH_2)_2$ | O |
| 91. | CH—$CH_2$<br>$CH_3$ | 7 | — | $(CH_2)_6$ | $C_6H_5CH_2$ | S |
| 92. | $CH_2CH$ | 8 | CH=CH | $(CH_2)_7$ | $C_6H_{13}$ | $\underset{\overset{\|}{O}}{\overset{\|}{S}}$ |
| 93. | $(CH_2)_2$ | 6 | CH=CH | $(CH_2)_8$ | $C_7H_{15}$ | $\underset{\overset{\|}{O}}{\overset{\overset{O}{\|}}{S}}$ |
| 94. | — | 2 | — | $(CH_2)_2$ | $C_2H_5$ | O |

What is claimed is:

1. A compound of the structure

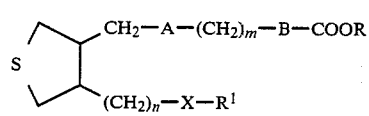

including all stereoisomers thereof, wherein A is $(CH_2)_2$, CH=CH or a single bond; B is a single bond or —CH=CH—; m is 1 to 8; n is 1 to 4; X is O or $$\underset{(O)_{n'}}{\overset{\overset{S}{\|}}{}}$$

wherein n' is 0, 1 or 2; R is H, lower alkyl or alkali metal; and $R^1$ is lower alkyl, aryl, arylalkyl, cycloalkyl, cycloalkylalkyl or lower alkenyl.

2. The compound as defined in claim 1 wherein A CH=CH and B is a single bond.

3. The compound as defined in claim 1 wherein X is O or S.

4. The compound as defined in claim 1 wherein m is 3 to 5 and n is 1.

5. The compound as defined in claim 1 wherein $R^1$ is H.

6. The compound as defined in claim 1 wherein B is a single bond, n is 1, A is CH=CH, X is O or S, n is 1, m is 3 to 5, R is H and $R^1$ is lower alkyl.

7. The compound as defined in claim 1 wherein $R^1$ is butyl, pentyl, hexyl or heptyl including all isomers thereof.

8. The compound as defined in claim 1 having the name [3α(Z),4α]-7-[4-[(hexyloxy)methyl]tetrahydro-3-thienyl]-5-heptenoic acid or the hexyl ester thereof, including all stereoisomers thereof.

9. The compound as defined in claim 1 having the name [3β(Z),4α]-7-[4-[(hexylthio)methyl]tetrahydro-3-thienyl]-5-heptenoic acid or its methyl ester including all stereoisomers thereof.

10. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

11. The method as defined in claim 11 wherein said compound is administered in an amount within the range of from about 1 to about 100 mg/kg.

12. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

13. A method of inhibiting platelet aggregation which comprises administering to a mammalian host an effective amount of a compound as defined in claim 1 or a pharmaceutically acceptable salt thereof.

14. A method of inhibiting bronchoconstriction associated with asthma, which comprises administering to a mammalian host an effective amount of a compound as defined in claim 1 or a pharmaceutically acceptable salt thereof.

15. A method for treating peripheral vascular disease, which comprises topically or systemically administering to a mammalian host an effective amount of a compound as defined in claim 1 or a pharmaceutically acceptable salt thereof.

16. A method for inhibiting platelet aggregation and bronchoconstriction by inhibiting production of thromboxane $A_2$ by blocking the action of thromboxane synthetase, which comprises administering to a mammalian host an effective amount of a compound as defined in claim 1 or a pharmaceutically acceptable salt thereof.

17. A method for treating inflammation in a mammalain species in need of such treatment, which comprises administering to a mammalian host an effective amount of a compound as defined in claim 1 or a pharmaceutically acceptable salt thereof.

18. A method of relieving pain in a mammalian specie, which comprises administering to said mammalian specie a composition containing an analgesically effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,542,151

DATED : September 17, 1985

INVENTOR(S) : Jagabandhu Das

It is certified that error appears in the above-identified patent and that said Letters Patent is hereby corrected as shown below:

Column 15, line 61, "ene2,3" should read --ene-2,3--.
Column 20, line 67, "155" should read --15%--.
Column 23, line 1, "IN" should read --1N--.
Column 24, line 22, "4β" should read --4α--.
Column 24, line 48, "4α" should read --4α]--.
Column 24, line 49, "thieny]" should read --thienyl]--.
Column 24, line 56, after "thienyl]" delete --3thienyl]--.
Column 26, line 15, "4[(" should read --4-[(--.
Column 28, line 6 should read --(3α,4α)-7-[4-[(Octylthio)-
  methyl]tetrahydro- --.
Column 29, line 12, "$P^{30}$" should read --$P^+$-- and "$Cl^{31}$"
  should read --$Cl^-$--.
Column 29, line 55, delete "cl" and start a new paragraph
  beginning with "C."
Column 30, line 14, "7-4-" should read --7-[4- --.
Column 31, line 67, "2-" should read --[2- --.
Column 32, line 44, "4-2-" should read --[4-[2- --.
Column 33, line 3, "nyl" should read --nyl]--.
Column 33, line 45, after "and" and before "except" insert --38--
Column 33, line 60, "4α" should read --4α]--.
Column 34, line 49, "4α" should read --4β--.
Column 34, line 52, "4α" should read --4β--.
Column 34, line 59, "4α" should read --4β--.
Column 35, line 53, "tetrahydro-b" should read
  --tetrahydro- --.

UNITED STATES PATENT AND TRADEMARK OFFICE
CERTIFICATE OF CORRECTION

PATENT NO. : 4,542,151          Page 2 of 2

DATED      : September 17, 1985

INVENTOR(S) : Jagabandhu Das

It is certified that error appears in the above-identified patent and that said Letters Patent is hereby corrected as shown below:

Column 36, line 2, "tetrahydro3" should read
  --tetrahydro-3--.
Column 36, line 37, after "tetrahydro-" insert -- 3- --.

Signed and Sealed this

Fourth Day of November, 1986

[SEAL]

Attest:

DONALD J. QUIGG

*Attesting Officer*       *Commissioner of Patents and Trademarks*